(12) United States Patent
Le

(10) Patent No.: US 11,751,665 B2
(45) Date of Patent: Sep. 12, 2023

(54) SYSTEM AND METHOD FOR AN EYE PATCH USED IN EYELASH EXTENSION PROCEDURE

(71) Applicant: Amazing Lash Franchise, LLC, Englewood, CO (US)

(72) Inventor: Jessica Le, Houston, TX (US)

(73) Assignee: Amazing Lash Franchise, LLC, Englewood, CO (US)

( * ) Notice: Subject to any disclaimer, the term of this patent is extended or adjusted under 35 U.S.C. 154(b) by 0 days.

(21) Appl. No.: 17/675,742

(22) Filed: Feb. 18, 2022

(65) Prior Publication Data

US 2022/0167728 A1 Jun. 2, 2022

Related U.S. Application Data

(62) Division of application No. 15/953,658, filed on Apr. 16, 2018, now Pat. No. 11,253,043.

(51) Int. Cl.
*A45D 7/00* (2006.01)
*A45D 44/00* (2006.01)
*A61F 9/04* (2006.01)

(52) U.S. Cl.
CPC .............. *A45D 44/00* (2013.01); *A61F 9/045* (2013.01)

(58) Field of Classification Search
CPC ...... A45D 44/12; A45D 44/00; A45D 44/002; A45D 40/30; A45D 2200/1009; A45D 2200/1018; A45D 2200/1027; A45D 2200/1036; A41G 5/02; A61F 9/045; A61F 12/12; A61M 35/006; A61M 35/10

See application file for complete search history.

(56) References Cited

U.S. PATENT DOCUMENTS

| | | | | |
|---|---|---|---|---|
| 2013/0247928 A1* | 9/2013 | Valucci | ................ | A45D 44/12 132/319 |
| 2014/0209114 A1* | 7/2014 | Johnson | ................ | A45D 37/00 132/319 |
| 2016/0058088 A1* | 3/2016 | Le | ........................... | A41G 5/02 132/201 |

* cited by examiner

*Primary Examiner* — Rachel R Steitz
(74) *Attorney, Agent, or Firm* — Polsinelli PC; Gregory P. Durbin

(57) ABSTRACT

An improved system and method for an eye patch can comprise a patch and a pad. The patch can be substantially flat and flexible. Furthermore, the patch can comprise a bottom surface, a top surface, and a concave edge. The bottom surface can comprise an adhesive capable of temporarily attaching to a skin. The concave edge can be on one side of the patch. Additionally, the concave edge can substantially match the anatomical curve of a human's eye socket. The pad can be a raised portion on the patch that can be capable of pushing upper natural eyelashes upward when a client closes her eyes. The pad can be attachable along the concave edge.

20 Claims, 9 Drawing Sheets

SYSTEM AND METHOD FOR AN EYE PATCH USED IN EYELASH EXTENSION PROCEDURE

CROSS-REFERENCE TO RELATED APPLICATION

This divisional application is related to and claims priority from U.S. application Ser. No. 15/953,658 filed Apr. 16, 2018 entitled "System and Method for an Eye Patch used in Eyelash Extension Procedure," the entire contents of which are fully incorporated by reference herein for all purposes.

BACKGROUND

This disclosure relates to a system and method for an eye patch used in an eyelash extension procedure.

An eyelash extension procedure involves bonding individual fake lashes to a person's natural lashes, one lash at a time. The procedure can usually involve applying an under eye patch to a client's eye, which can cover the lower lashes while hydrating and relaxing the under eye. Furthermore, such procedure separates the bottom natural lash lashes from the top natural lashes of the client's eyes. Though such procedure helps in preventing lower lashes from interfering with upper lashes during eyelash extension procedure, it does little to aid the eyelash technician in applying individual fake lashes to natural lashes of the client.

Thus, having a raised portion at an edge of the eye patch can be advantageous and can aid in pushing the client's eyelashes upwards. By pushing eyelashes upwards, upper natural lashes can spread outwards, which can help the eyelash technician to access each natural lashes lash of the client. As such, it would be useful to have an improved system and method for an eye patch.

SUMMARY

An improved system and method for an eye patch can comprise a patch and a pad. The patch can be substantially flat and flexible. Furthermore, the patch can comprise a bottom surface, a top surface, and a concave edge. The bottom surface can comprise an adhesive capable of temporarily attaching to a skin. The concave edge can be on one side of the patch. Additionally, the concave edge can substantially match the anatomical curve of a human's eye socket. The pad can be a raised portion on the patch that can be capable of pushing upper natural eyelashes upward when a client closes her eyes. The pad can be attachable along the concave edge.

The method for applying an eye patch for an eyelash extension procedure comprising the step of placing an eye patch onto a client's eye area. The eye patch can comprise a patch and a pad. The patch can be substantially flat and flexible. Furthermore, the patch can comprise a bottom surface, a top surface, and a concave edge. The bottom surface can comprise an adhesive capable of temporarily attaching to a skin. The concave edge can be on one side of the patch. Additionally, the concave edge can substantially match the anatomical curve of a human's eye socket. The pad can be a raised portion on the patch that can be capable of pushing upper natural eyelashes upward when a client closes her eyes. The pad can be attachable along the concave edge. The method can also comprise the step of pushing said upper natural lashes upwards through placement of said pad.

DETAILED DESCRIPTION

Described herein is an improved system and method for an eye patch used in eyelash extension procedure. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
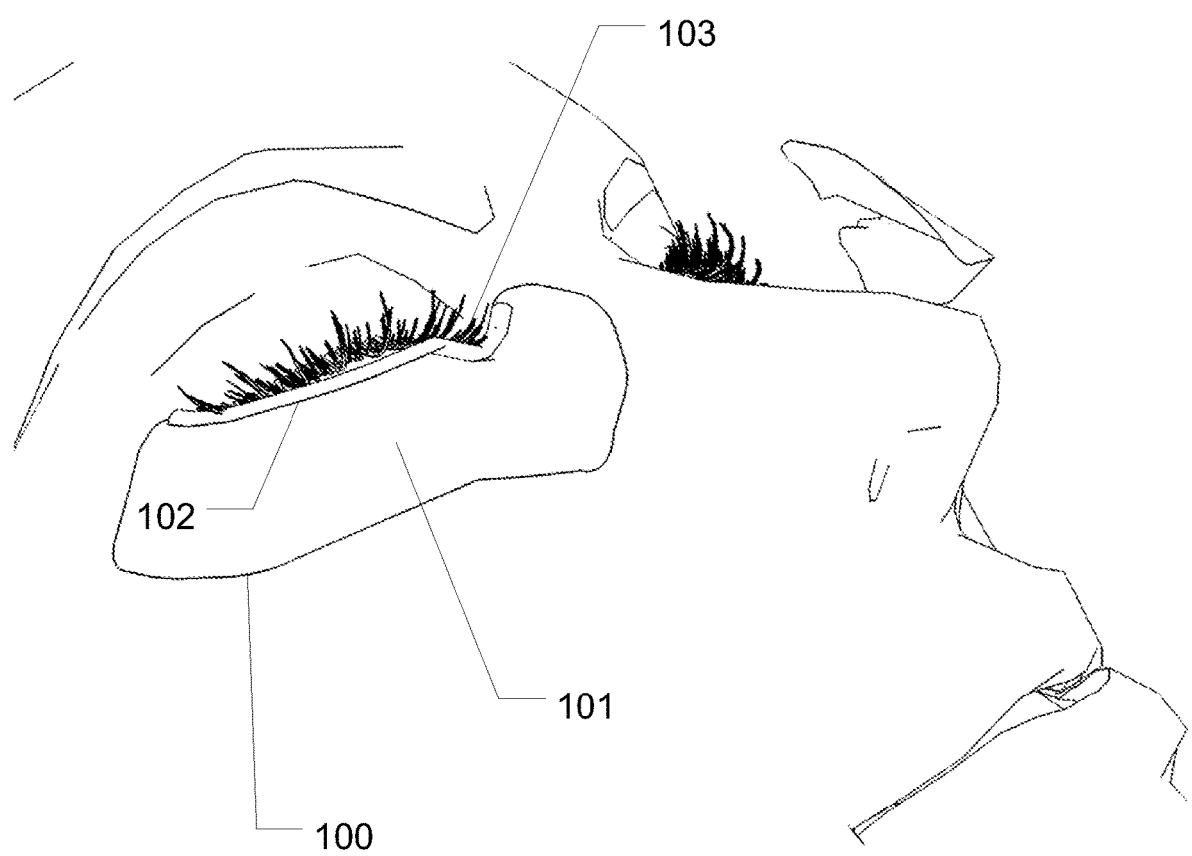
FIG. 1 illustrates an eye patch being used during an eyelash extension procedure.

FIG. 1 illustrates an eye patch 100 being used during an eyelash extension procedure. In a preferred embodiment, eye patch 100 can be an under eye patch that is used to protect and hold lower lashes during eyelash extension procedure. Eye patch 100 can comprise a patch 101, and a pad 102. Patch 101 can be the portion of eye patch 100 that comes in contact with a client's skin while pad 102 can be the portion of eye patch 100 that comes in contact with the client's lashes. In an embodiment wherein eye patch 100 can be an under eye patch, eye patch 100 can further comprise a concave edge 103 that is compatible under the eye area of the client. Concave edge 103 can substantially match the anatomical curve of a human's eye socket. Further in one embodiment, eye patch 100 can be used as an eye mask, or eye gel that can relax and/or treat the eye area while the client is going through the eyelash extension process. As such, eye patch 100 can comprise of eye treatment materials such as collagen, Arbutin, etc., which can provide moisture and relaxes the eye. Pad 102 can be a thick piece of soft material such as rubber, foam, and/or fabric. Pad 102 can be a raised portion on eye patch 100, which can push upper natural eyelashes upward when a client closes her eyes. Moreover, pad 102 can be in various thickness, size, and/or shape. In one embodiment, pad 102 can be an elongated thick strip that can be contoured along concave edge 103. In such embodiment, an eyelash technician needs to manually contour pad 102 to match concave edge 103. In another embodiment, pad 102 can be prefabricated. Thus, pad 102 can already be in a curved shape that matches concave edge 103. In such embodiment, the eyelash technician does not need to contour pad 102 when attaching pad 102 along concave edge 103.

Figure 2:
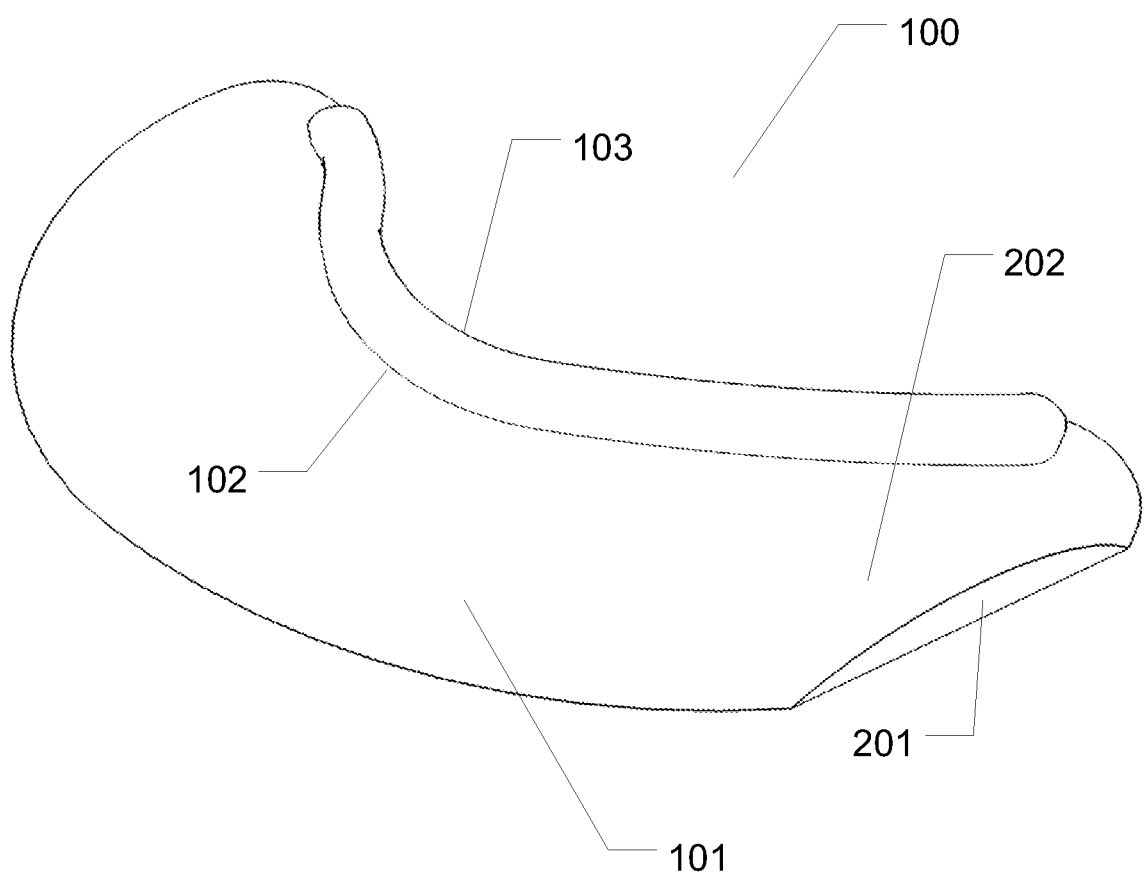
FIG. 2 illustrates an eye patch comprising a patch and a pad.

FIG. 2 illustrates an eye patch 100 comprising patch 101 and pad 102. Patch 101 can be a flat piece of material that can cover a substantial area around the eye. Patch 101 can comprise a bottom surface 201 and a top surface 202. Bottom surface 201 can be the portion of eye patch 100 that is placed onto the client's skin and/or around eye area. In one embodiment, bottom surface 201 can comprise a skin adhesive that can allow eye patch 100 be temporarily placed onto the desired area of the client's skin. In an embodiment wherein eye patch 100 can be an eye mask or an eye gel, bottom surface 201 can be capable of adhering onto the client's skin. Further, top surface 202 can be the exposed portion of eye patch 100. Pad 102 can be attached at top surface 202 along concave edge 103 of eye patch 100. In one embodiment, patch 101 can be permanently attached to pad 102 through a method that includes but is not limited to adhesion, molding, and sewing. In another embodiment, pad 102 can be unibody with patch 101. As such, pad 102 and patch 101 can be a single device.

Figure 3:
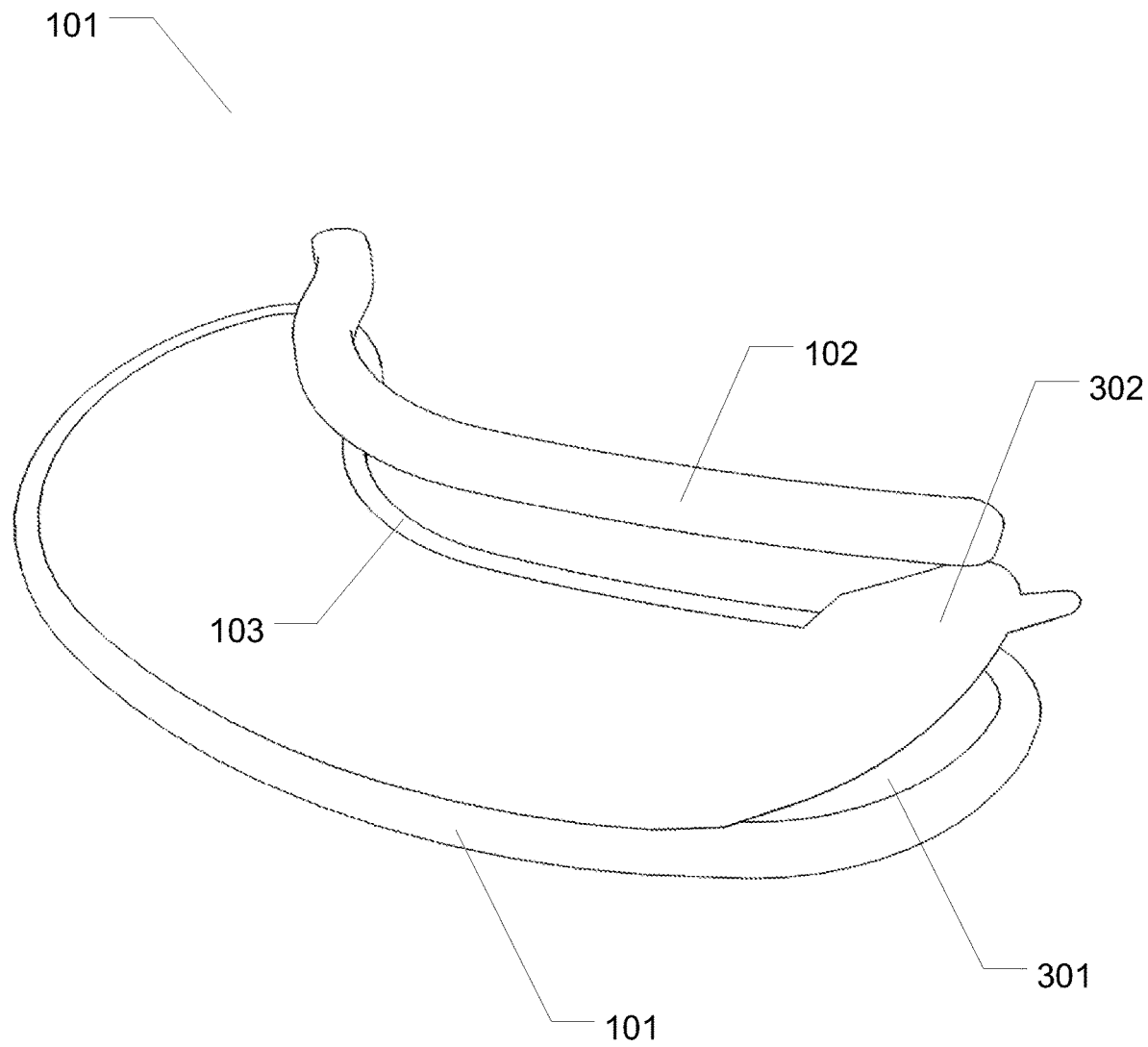
FIG. 3 illustrates an embodiment of a patch comprising an adhesive material.

FIG. 3 illustrates an embodiment of patch 101 comprising an adhesive material 301 and a backing 302. Adhesive material 301 can be any substance capable of binding patch 101 with pad 102. Backing 302 can be used to temporarily cover adhesive material 301 and prevent particles from attaching onto adhesive material 301. Backing 302 can be made of coated paper, or plastic that can allow backing 302 to be peeled off from adhesive material 301. In this embodiment, adhesive material 301 can cover top surface 202. Thus, adhesive material 301 can be positioned along concave edge 103 of patch 101. Backing 302 can be removed from adhesive material 301. Once removed, pad 102 can be placed along concave edge 103. In an embodiment wherein patch 101 and pad 102 can be a single device, adhesive material 301 can only cover top surface 202 below pad 102.

Figure 4:
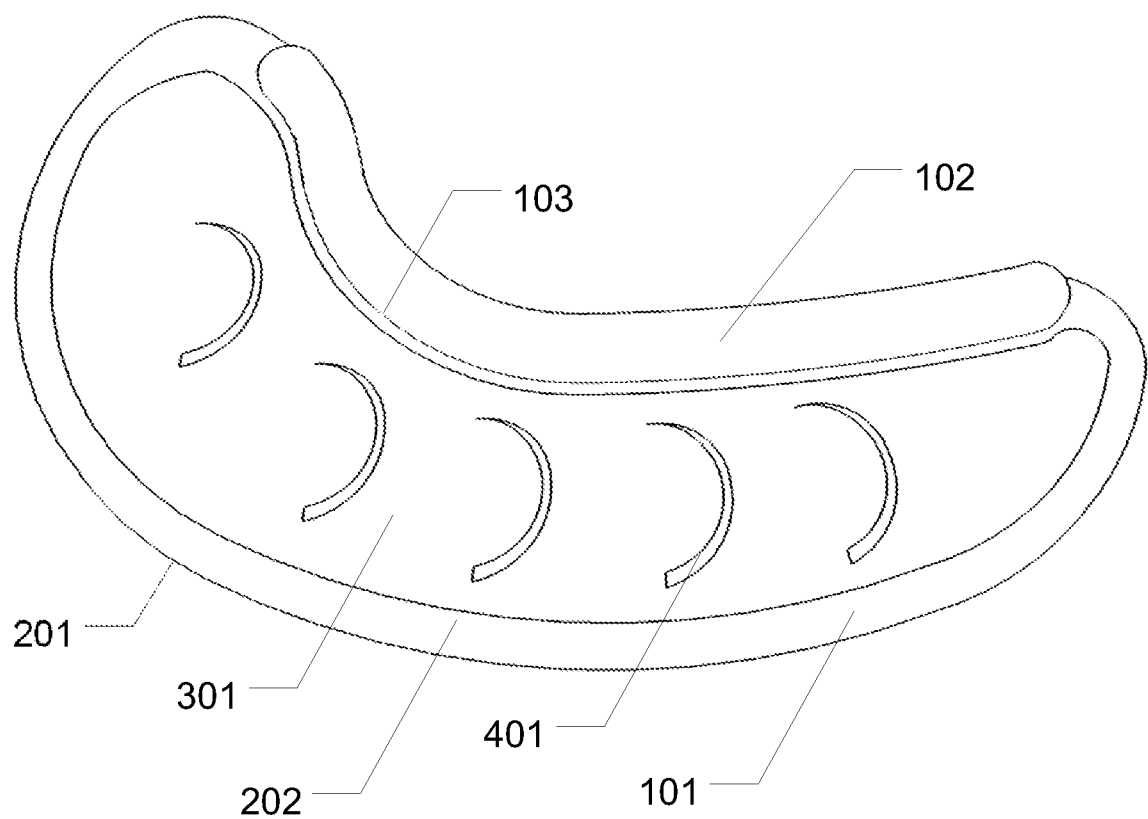
FIG. 4 illustrates an embodiment of a patch covered with an adhesive material.

FIG. 4 illustrates an embodiment of patch 101 covered with adhesive material 301. In this embodiment, adhesive material 301 can cover entire top surface 202 of patch 101. In this embodiment, concave edge 103 can secure pad 102 while the exposed top surface 202 of patch 101 can be used to temporarily hold a plurality of loose extension eyelashes 401.

Figure 5:
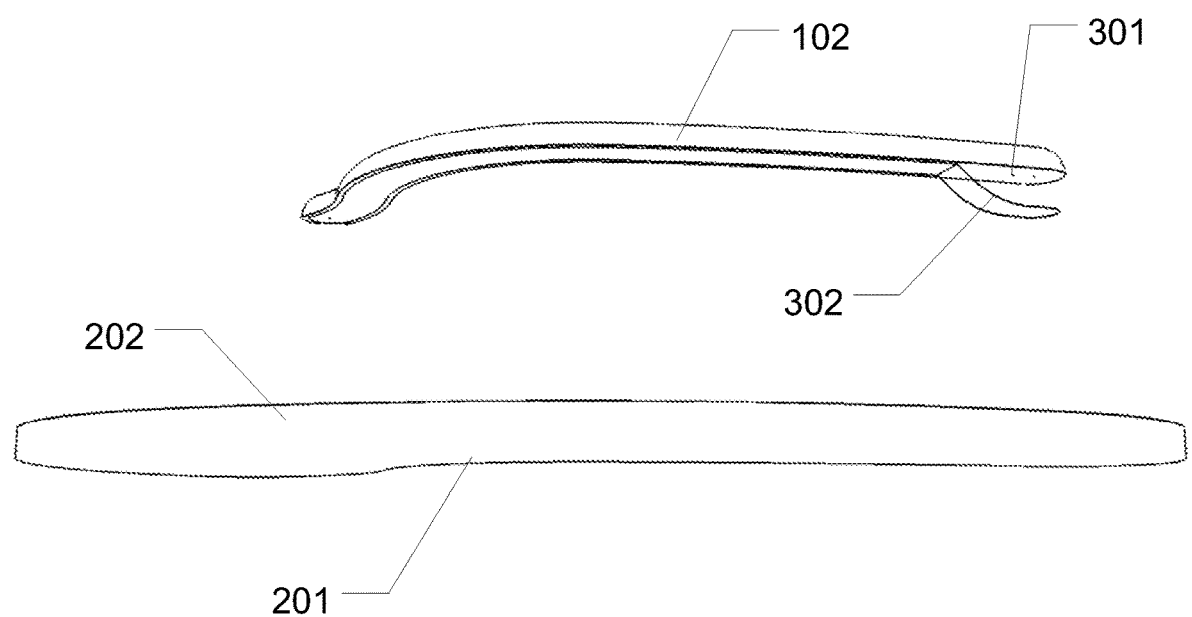
FIG. 5 illustrates an embodiment of pad comprising an adhesive material.

FIG. 5 illustrates an embodiment of pad 102 comprising adhesive material. In such embodiment, the bottom surface of pad 102 can comprise adhesive material 301 and backing 302. In this embodiment, backing 302 can be removed from pad 102 to expose adhesive material 301. As such, the eyelash technician applying eyelashes can place pad 102 on top surface 202 of patch 101.

Figure 6A:
FIG. 6A illustrates an eye patch placed under the eye of a client.

FIG. 6A illustrates eye patch 100 placed under the eye of the client. Initially, the area surrounding the eye of the client can be cleansed. Next, patch 101 can be positioned under the eye of the client, such that concave edge 103 can hold down lower lashes of the client. As such, bottom surface 201 can adhere onto the client's under eye area.

Figure 6B:
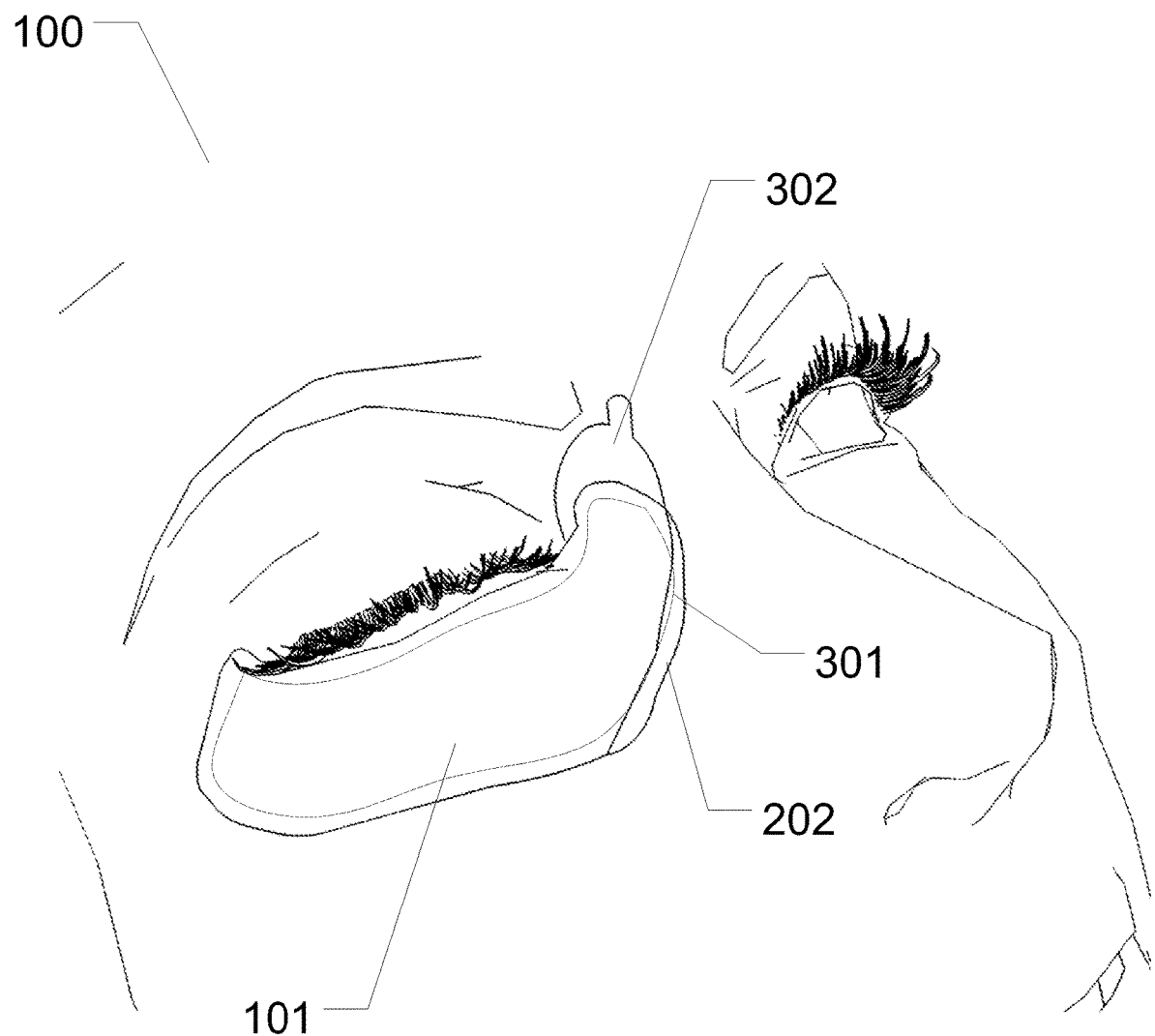
FIG. 6B illustrates a backing being peeled off a patch.

FIG. 6B illustrates backing 302 being peeled off from patch 101. In an embodiment wherein adhesive material 301 covers the entire patch 101, backing 302 can be removed from entire top surface 202 to expose adhesive material 301. Further, in an embodiment wherein patch 101 and pad 102 can be a single device, backing 302 can be removed from top surface 202 below pad 102.

Figure 6C:
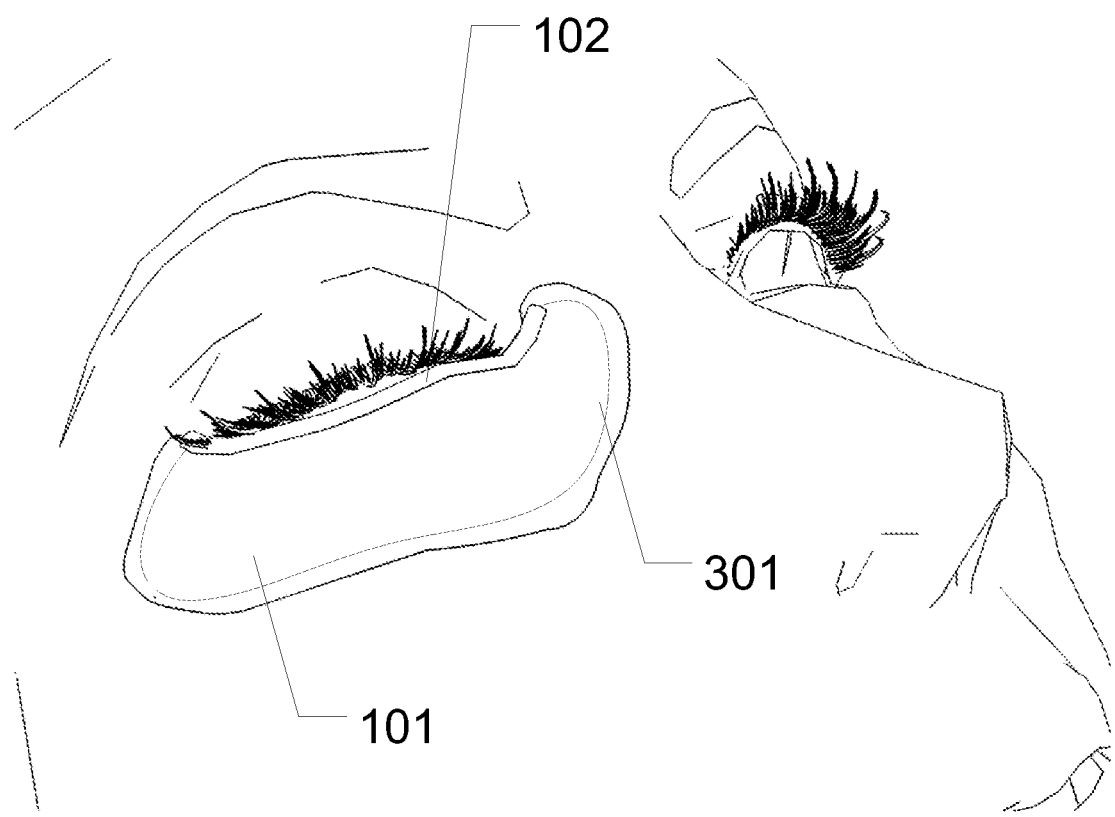
FIG. 6C illustrates a pad placed on a patch.

FIG. 6C illustrates pad 102 placed on patch 101. After backing 302 is removed, pad 102 can then be positioned and attached along concave edge 103. In an embodiment wherein adhesive material 301 can be on pad 102, backing 302 can first be peeled off from pad 102 before attaching pad 102 along concave edge 103. Pad 102 can be placed along concave edge 103 such that natural lashes of the client can be cushioned and can be raised upward as the client closes her eyes. As natural upper lashes are pushed upwards, the upper lashes can spread outwards making the natural upper lashes of the client be more accessible for the technician. In one embodiment, the technician can comb the natural upper lashes to ensure that upper lashes are smooth and separated. Once eye patch 100 is in place, the technician can begin with eyelash extension procedure. Initially, using tweezers, the technician can grab one of loose extension lashes 401 and dip a tip of loose extension lashes 401 into glue. Next, using another hand, the technician can isolate a single natural upper lash of the client and attach one of loose extension lashes 401 to said single natural upper lash. The same procedure can be done repeatedly until a complete set of loose extension lashes 401 are applied on the client's natural eyelashes.

Figure 6D:
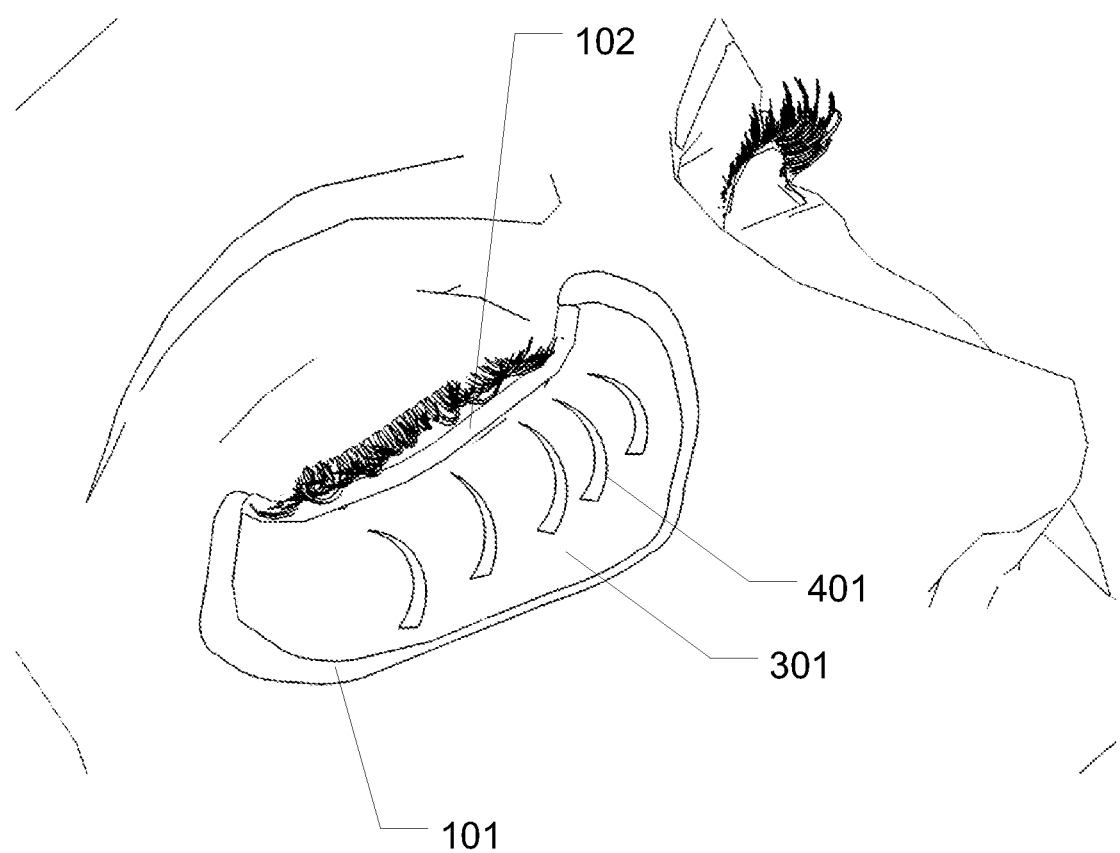
FIG. 6D illustrates an eye patch supporting a plurality of loose extension lashes.

FIG. 6D illustrates eye patch 100 supporting loose extension eyelashes 401. Loose extension eyelashes 401 can be attached along adhesive material 301 on top surface 202. Further, the embodiments wherein patch 101 and pad 102 can be a separate device can allow user to adjust, cut, and/or trim patch 101 and/or pad 102 separately to ensure that eye patch 100 can custom fit a specific client. As such, patch 101 can be trimmed to custom fit the client's eye area. Pad 102 can then be adjusted and attached along concave edge 103. Lastly, excess portion of pad 102 that can extend outside concave edge 103 can be cut.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed:

1. A method for an eyelash extension procedure, the method comprising:
  applying an eye patch onto a client, wherein the eye patch is comprised of a patch and a pad, the patch substantially flat and flexible, the patch further comprising:
    a bottom surface and a top surface, the bottom surface comprising a bottom adhesive material capable of temporarily attaching to the client's skin; and
    a concave edge on one side of the patch, wherein the concave edge substantially matches an anatomical curve of a human's eye socket;
  adhering the patch to the client's skin, wherein the bottom adhesive material on the bottom surface is exposed and temporarily attaches to the client's skin, wherein the patch covers lower lashes of the client; and attaching the pad on the top surface of the patch along the concave edge of the patch, wherein the pad is attachable along the concave edge, the pad being a raised portion on the patch that is capable of pushing upper natural eyelashes upward when the client's eyes are closed.

2. The method of claim 1, wherein a majority portion of the top surface comprises a top adhesive material, the top adhesive material capable of binding the pad along the concave edge of the top surface.

3. The method of claim 2, further comprising:
removing one or more backings from the top adhesive material before binding the pad onto the top surface, wherein the one or more backings are capable of covering the top adhesive material.

4. The method of claim 3, further comprising:
supporting at least one loose extension eyelash on the top adhesive material.

5. The method of claim 4, further comprising:
grabbing at least one of the loose extension eyelashes from the top adhesive material of the patch;
dipping a tip of the loose extension eyelash into a glue; and
isolating a single natural upper eyelash on the client and attaching at least one of the loose extension eyelashes to the single natural upper eyelash on the client.

6. The method of claim 1, further comprising:
trimming the patch to custom fit the client's eye area;
adjusting the pad along the concave edge to substantially contour the client's eye; and
removing an excess portion of the eye patch.

7. The method of claim 1, wherein the patch and the pad are a unibody component.

8. The method of claim 1, wherein the bottom adhesive material on the bottom surface contains an eye treatment material that can provide topical treatment to the client's eye area.

9. The method of claim 1, wherein the pad comprises a first surface, the first surface comprising an adhesive material capable of binding the pad to the top surface of the patch.

10. The method of claim 9, further comprising:
removing a pad backing from the adhesive material on the first surface before binding the pad onto the top surface, wherein the pad backing is capable of covering the adhesive material on the first surface.

11. The method of claim 1, wherein the pad is further comprised of a material including at least rubber, foam, or fabric.

12. The method of claim 1, further comprising:
removing one or more bottom backings from the bottom adhesive material before applying the eye patch onto the client, wherein the one or more bottom backings are capable of covering the bottom adhesive material.

13. A method for an eyelash extension procedure, the method comprising:
applying an eye patch onto a client, wherein the eye patch is comprised of a patch and a pad, the patch substantially flat and flexible, the patch further comprising:
a bottom surface and a top surface, the bottom surface comprising a bottom adhesive material capable of temporarily attaching to the client's skin; and
a concave edge on one side of the patch, wherein the concave edge substantially matches an anatomical curve of a human's eye socket; and
adhering the eye patch to the client's skin, wherein the bottom adhesive material on the bottom surface is exposed and temporarily attaches to the client's skin and the concave edge of the patch substantially contours the client's eye area, wherein the patch covers lower lashes of the client and the pad is capable of pushing upper natural eyelashes upward when the client's eyes are closed.

14. The method of claim 13, wherein a majority portion of the top surface comprises a top adhesive material, the top adhesive material capable of removably binding at least one loose extension eyelash to the top surface.

15. The method of claim 14, further comprising:
removing one or more backings from the top adhesive material on the top surface before binding the loose extension eyelash to the top surface, wherein the one or more backings are capable of covering the top adhesive material.

16. The method of claim 14, further comprising:
grabbing at least one of the loose extension eyelashes from the top adhesive material of the patch;
dipping a tip of the loose extension eyelash into a glue; and
isolating a single natural upper eyelash on the client and attaching at least one of the loose extension eyelashes to the single natural upper eyelash on the client.

17. The method of claim 13, further comprising:
trimming the patch to custom fit the clients eye area; and
removing an excess portion of the eye patch.

18. The method of claim 13, wherein the bottom adhesive material on the bottom surface contains an eye treatment material that can provide topical treatment to the client's eye area.

19. The method of claim 13, wherein the pad is further comprised of a material including at least rubber, foam, or fabric.

20. The method of claim 13, further comprising:
removing one or more bottom backings from the bottom adhesive material before applying the eye patch onto the client, wherein the one or more bottom backings are capable of covering the bottom adhesive material.

* * * * *